(12) United States Patent
Resh

(10) Patent No.: US 9,891,205 B2
(45) Date of Patent: Feb. 13, 2018

(54) WATER CHEMISTRY TEST KIT APPARATUS AND RELATED METHODS

(71) Applicant: Eric V. Resh, Temecula, CA (US)

(72) Inventor: Eric V. Resh, Temecula, CA (US)

( * ) Notice: Subject to any disclaimer, the term of this patent is extended or adjusted under 35 U.S.C. 154(b) by 0 days.

(21) Appl. No.: 14/215,810

(22) Filed: Mar. 17, 2014

(65) Prior Publication Data
US 2014/0342461 A1    Nov. 20, 2014

Related U.S. Application Data

(60) Provisional application No. 61/800,418, filed on Mar. 15, 2013.

(51) Int. Cl.
*G01N 33/18* (2006.01)
*G01N 31/22* (2006.01)

(52) U.S. Cl.
CPC .......... *G01N 33/182* (2013.01); *G01N 31/22* (2013.01); *Y10T 436/193333* (2015.01)

(58) Field of Classification Search
CPC ....... Y10T 436/00; Y10T 436/12; G01N 1/00; G01N 1/01; G01N 2001/027; G01N 33/18; G01N 33/1813; G01N 33/182; G01N 33/52
USPC ........ 436/125, 124; 422/430, 50; 73/52, 863
See application file for complete search history.

(56) References Cited

U.S. PATENT DOCUMENTS

| | | | | |
|---|---|---|---|---|
| 4,432,763 A | * | 2/1984 | Manschot | A61J 1/10 128/DIG. 24 |
| 4,663,126 A | * | 5/1987 | Gould et al. | 422/417 |
| 5,525,475 A | * | 6/1996 | Ladouceur | G01N 33/5302 210/634 |
| 6,506,346 B1 | * | 1/2003 | Monro | B01L 3/502 422/544 |
| 2003/0147568 A1 | * | 8/2003 | Edwards | B65D 33/02 383/119 |
| 2010/0054636 A1 | * | 3/2010 | Owensby | B65D 33/004 383/38 |

* cited by examiner

*Primary Examiner* — Christine T Mui
(74) *Attorney, Agent, or Firm* — J. Mark Holland + Associates; J. Mark Holland; Alison Adnan

(57) ABSTRACT

Methods and apparatus are disclosed for an improved water chemistry test. Features disclosed include, without limitation, a test block, colored liquid reagents, and color comparison displays, with test chambers/vials that are generally horizontal. The mouth at the top of each vial is formed along a substantial portion of the vial's horizontal length. The vial's horizontal dimensions enable water to move throughout each vial so that a wave or waves roll from one side of the vial to the other and quickly/thoroughly mixes colored liquid reagents with sample water. At least one ridge, wall, semipermeable barrier, etc. within the vial causes water and chemical reagents to more quickly and thoroughly when the test block is agitated. At least one drain hole is positioned in a wall/side of each vial, with its bottom edge located at the fill level necessary to conduct the water sample. A valve or valves enables a user to easily drain sample water from the vial down to the proper test level. An additional element at or near the top of at least one side of each vial serves to deflect the wave(s) of water and prevent them from splashing out of the vial through the vial's mouth. Adjacent to each vial is a color comparison display. The test block base allows it to be freestanding.

17 Claims, 3 Drawing Sheets

WATER CHEMISTRY TEST KIT APPARATUS AND RELATED METHODS

This application is based on and claims priority to U.S. provisional application Ser. No. 61/800,418, filed Mar. 15, 2013.

This invention relates broadly to devices for maintaining swimming pools, spas, fountains, water tanks and similar water features, and more specifically is directed to apparatus and methods involving an improved water chemistry test kit useful for (among other things) testing swimming pool water. As indicated herein, the inventions disclosed herein can be used in a broad range of applications and provide many benefits.

These and other embodiments will become readily apparent to those skilled in the art from the following detailed description of embodiments having reference to the attached figures, the invention not being limited to any particular preferred embodiment(s) disclosed.

BACKGROUND OF THE INVENTION

Many prior art water chemistry test kits used for maintaining swimming pools, spas, fountains, water tanks, etc. consist of, among other things, a vial or vials, colored liquid reagents, and color comparison displays or charts. More recently and commonly used in the swimming pool industry and other industries are devices that are sometimes called 'test blocks,' in which two vials (typically one vial is used for testing chlorine levels and the other primarily for testing acid levels) are molded vertically together as one single unit, with corresponding colored comparison displays. Some examples of such test blocks are the Guardex 4-in-1 Test Kit (shown generally at http://swimmingpoolproducts.halogensupply.com/viewitems/pool-spa-test-kits-testing-supplies/guardex-4-in-1-pool-test-kits-reagents, although current displays of products on that website may not qualify as prior art with respect to the current inventions) and the Taylor Test Kits (shown generally at http://www.taylortechnologies.com/pool-spa.asp, although current displays of products on that website may not qualify as prior art with respect to the current inventions).

Prior art 'test blocks' have been used for several decades, but are the outgrowth of earlier swimming pool reagent test kits that originally were comprised of individual components, such as (a) glass test tube vials, (b) a holder to prevent spilling by keeping test tubes vertical, and (c) separate colored comparison displays. The test tubes typically were narrow vertical transparent cylinders or vials that were closed at the bottom and open at the top, and prior art test blocks include similar vertical test tube/vials of similar design, that have been combined with a base or other element that enable the vials/tubes to be conveniently positioned to be relatively vertical oriented and freestanding.

The relevant prior art test tubes generally have had smooth sides, a single opening that forms a mouth, with the mouth's opening being as wide or wider than the vial's body. The more recent prior art "test blocks" have replicated these "test tube" design features also, although some have vials with a generally rectangular or square cross-section formed by having generally flat elongated vertical sides instead of the rounded sides commonly found on glass test tubes. Additional features on some prior art test blocks are such things as fill lines, chemical names, and other indicia that are either molded into or printed onto the plastic vial(s) or block.

Colored comparison displays are commonly molded into the prior art block(s) adjacent to a corresponding vial (i.e. gradients of yellow plastic next to the chlorine test vial, etc.) and because the tests typically involve a visual evaluation of the color of the tested liquid, having the "color measuring scale" built into the container enables a user to easily compare the water being tested in the vial to the "standard" color display.

Vial caps likewise are commonly provided in prior art systems, to seal the liquids within the vials, and all components (test block, reagent liquids, caps, instructions, etc.) are usually packaged together as a "test kit" in a plastic, chemical resistant container.

Typically, in using a reagent test kit to test water in a swimming pool or other water feature, a user must take the following steps:

1. Submerge the test block several inches below the water's surface (18 inches is recommended to ensure that the sample is representative of the entire pool, rather than just the surface water which may have some local anomalies).

2. Turn the submerged test block so that the vials' openings are pointed upward (this allows air to escape and water to fill the vials).

3. Lift the test block with filled vials out of the water.

4. Adjust the water level in the vial to the fill line marker on the vial (this typically is done by just tipping the unit slightly and then shaking or tapping the test block to pour out enough of the water to drop the level to the desired test volume).

5. Put reagent (chemicals) into the water sample. This is typically done by squeezing a dropper containing colored liquid reagent until a designated number of reagent drops fall into the sample water in the indicated vial(s). For the test to be effective and meaningful, relative proportions of water sample and the reagent must be relatively precise. Prior art devices and systems accomplish this control of proportions by requiring the user to accurately control the volume of the water sample and the number of reagent drops put into that sample (as more thoroughly discussed below).

6. Shake or tap the test block repeatedly to mix the reagent and water thoroughly within the vertical vial (this is done until all the water in the vial has a chance to change color). The properties of the water being tested will determine the resulting color of the mixed reagent/water sample, thereby permitting the user to make the desired visual "measurement" described in the next step.

7. Make a visual comparison between the colored display and the test water in the vial.

Often vials have minor directives or comments or reminders (such as 'Ideal" or "Add Acid") to assist a user in determining a proper course of action after completing the water test.

Despite their usefulness, there are several problems associated with prior art test blocks. Some problems occur as a result of the vials being relatively narrow, elongated and vertical. For example, after being submerged, filled with water, and lifted from the pool, lowering the vial's water level to the fill line requires a user to shake, tap, or pour out excess water. This is generally not a very precise operation, and these efforts to get to the "correct" test water volume frequently results in too much water being removed from the vial. When this occurs, the "fill" steps of the process must be done again (otherwise the proportion of water to test chemicals will not be proper), starting with resubmerging the vial into the pool. There is no guarantee that the second attempt to properly fill the vial will be any more successful than the first, and it is not at all uncommon for three or four attempts to be needed in obtaining the correct amount of water in the vial. Such imprecise control and resulting unpredictability not only can be time consuming and inconvenient, but it is further frustrating when the user is in a hurry or must repeatedly dip his/her arm into a pool or other body of water that is exceptionally cold. Having two vials to fill (which is common in many test blocks) multiplies these problems/issues.

Another problem arises when colored reagent drops are added to the test water in the vial. Given the relatively small size of the droppers and vials and the conditions in which the testing is sometimes done (e.g., outdoors, in inclimate weather, etc.), it can be easy to miss or partially miss the narrow mouth of prior art vials or test blocks when dispensing the drops of testing chemicals from the dropper into the vial(s). Among other things, this can result in a user losing count of the number of drops added from the dropper to the vial and, consequently, having to do the test again from the beginning.

Furthermore, drops that successfully land in the vial do not always readily mix with the water in the vial. Even when being tapped or shaken, at least some of the prior art vials are so elongated and narrow that the shape seems to hinder or at least does not readily facilitate moving or stirring the water within them, so a user may need to take the additional step of placing a cap on the vial so that it can be shaken more vigorously (to accomplish the necessary mixing of the chemicals into the water being tested). Vial caps are typically available as part of such prior art systems, but being small and often loosely packaged in the test kit, the caps are easily lost or contaminated. One convenient alternative to such caps is to use one's finger or hand to cover the vial while shaking and mixing the chemical into the water, but that "finger" approach also risks contaminating the water sample or otherwise distorting the proportions of water/reagent, and can therefore result in an inaccurate test reading.

For at least these reasons, the narrow and elongated vertical vials of prior art test blocks have many inconveniences that slow down, interrupt, and even contaminate the water testing process.

DETAILED DESCRIPTION OF EMBODIMENTS

Figure 1:
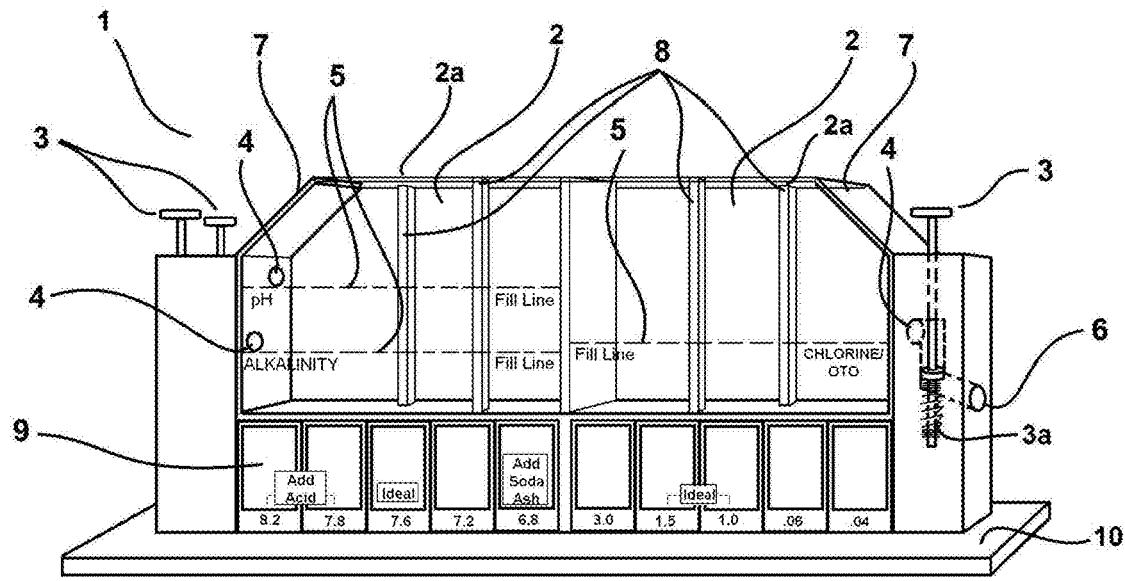
FIG. 1 is an elevation perspective view of one of the many embodiments of a test block constructed in accordance with the current invention.
Figure 1A:
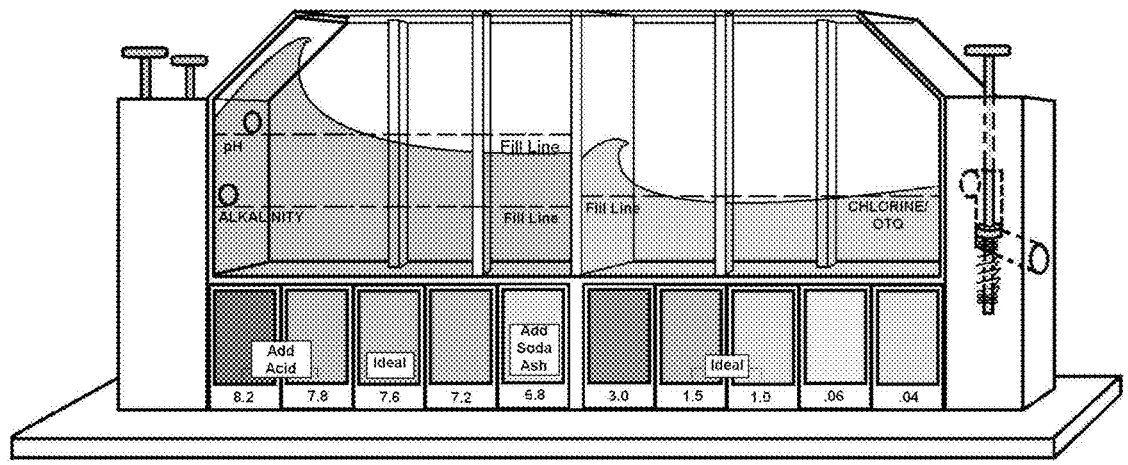
FIG. 1A is similar to FIG. 1, but includes liquids inside the test sections within the block, in various colors.

As indicated above, the inventions disclosed herein can be used in a broad range of applications and provide many benefits. Embodiments of the present invention will now be described with references to the accompanying figures, wherein like reference numerals refer to like elements throughout.

Persons of ordinary skill in the art will understand that the apparatus of the invention and variations of its many methods can be practiced using any of a wide variety of suitable processes and materials. By way of example and not by way of limitation, certain embodiments of the apparatus can be manufactured via processes using one or more steps of injection molding, gluing, bonding, shaping, milling, drilling, injection molding, thermo-forming, casting, and many other existing and new processes that may come into being. Materials are not limited in any way and could extend to include at least certain parts of the apparatus being made from metals to plastics, to resins of all types. A preferred material is lightweight, non-corrosive and will hold up to the exposure anticipated in its eventual usage (including by way of example, chemical reagents, chlorinated water, acidic water, salt water, marine environments, UV exposure, etc.). A preferred method of manufacture is by injection molding and coloring various components of the embodiments, and by machining others and/or buying them from commercially-available sources.

Figure 2:
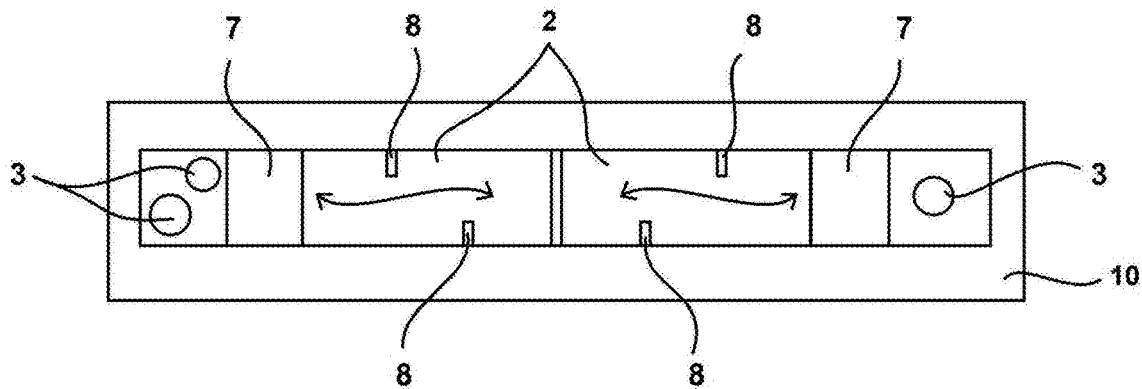
FIG. 2 is a top view of the embodiment of FIG. 1.

Referring now to the drawings, and particularly to FIGS. 1 and 2, a preferred embodiment of a test block 1 used for testing the chemistry of water in swimming pools is shown, including one or more vials 2 with mouth openings 2a designed to hold generally horizontal bodies of sample water to be tested for chemicals. One or more fill lines 5 indicate desired fill levels appropriate for testing. One or more drain holes 4 located on inside walls of the vials are positioned with their lowest edges at or near the desired fill levels and allow excess water to drain out of vials through drain ports 6. One or more valves 3 controlling the flow of water through drain holes and drain ports are easily accessible and may be readily opened or closed as needed, and may further include a valve spring 3a or other device(s) to help them move between open and closed positions. Persons of ordinary skill in the art will understand that the water-levelling structures and "automating" elements discussed herein may be provided and fabricated and used in any of a wide variety of embodiments, all without departing from the scope of the invention.

In the embodiments illustrated in FIGS. 1 and 2, the horizontal design of the vials as well as other features shown and discussed herein enable water samples and colored chemical reagents inside vials to be quickly and easily mixed together to allow more accurate, quicker, and easier testing via mixing the chemicals. For example, preferably the chemicals and water simply mix better because of their preferred generally horizontal orientation as the user agitates/rolls/moves/etc. the block from side to side (or via tilting, rocking, shaking, etc.). In certain embodiments, one or more deflection barriers 7 of an appropriate size/shape/position are provided to help prevent water samples from splashing out of the mouth of each vial (persons of ordinary skill in the art will understand that, among the many alternative embodiments of the invention, such barriers can be movable, horizontal, covering all or some of the opening(s) 2a, etc.). The rolling/moving water and chemical reagents can be further urged to mix together in embodiments that include ridges/walls/barriers or other elements or means 8 that cause and/or increase the desired mixing turbulence within the rolling/moving water. Although mixing means 8 are illustrated in FIGS. 1 and 2 as being generally vertical rectangular elements extending all or virtually the full height of the vial(s) 2, persons of ordinary skill in the art will understand that, among the many alternative embodiments of the invention, such mixing/agitating elements can be provided in a wide range of configurations, including (by way of example and not by way of limitation) mesh structures, a plurality of elements spaced from each other vertically and/or horizontally, tapered/rounded cross-sections, etc.).

Figure 3:
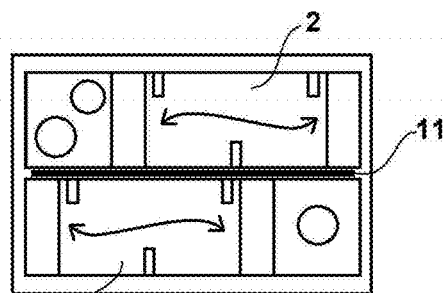
FIG. 3 is a top view of one of the many alternative embodiments of the invention.
Figure 4:
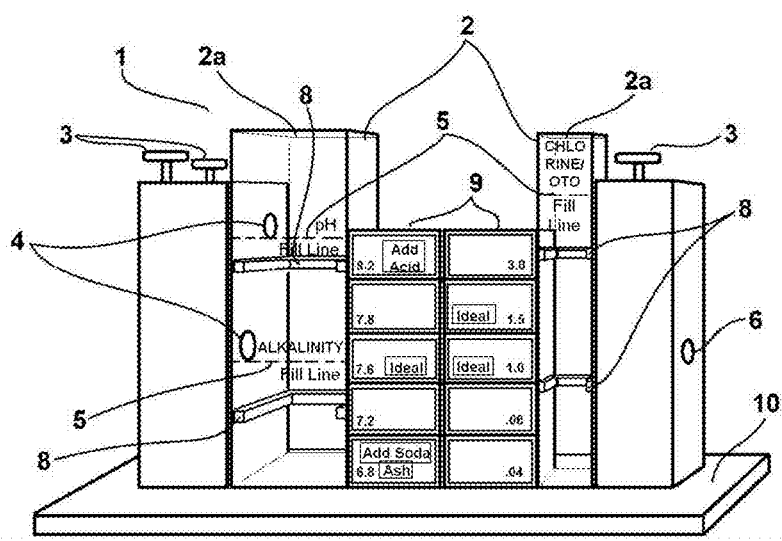
FIG. 4 is similar to FIGS. 1 and 1A, but shows an embodiment with:
 a. vertical vials with adjacent vertical colored comparison display
 b. drain holes at fill lines
 c. valves
 d. mixing ridges/walls/barriers
Figure 5:
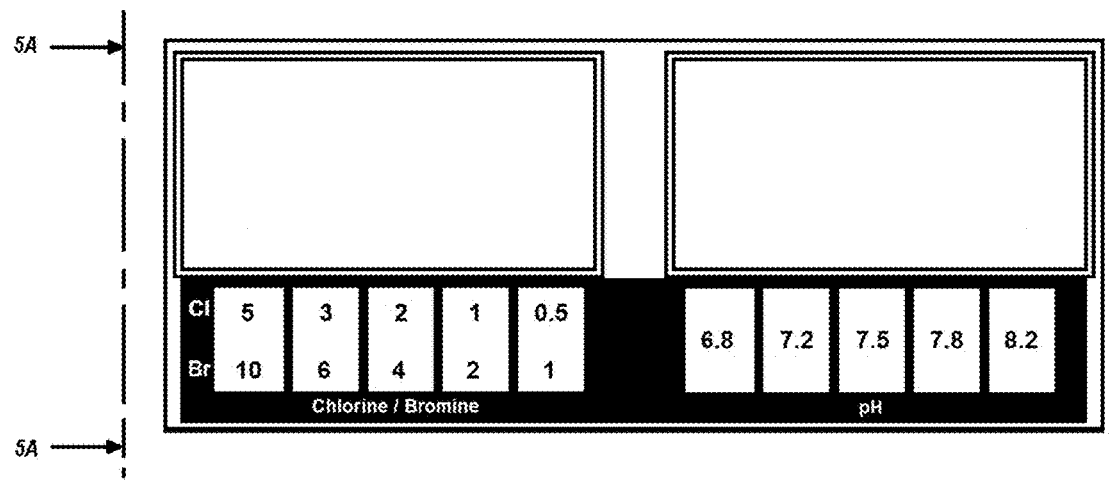
FIG. 5 is a top view of an embodiment of the invention, illustrating a test kit with broad and/or planar vials (similar to a petri-dish).
Figure 5A:
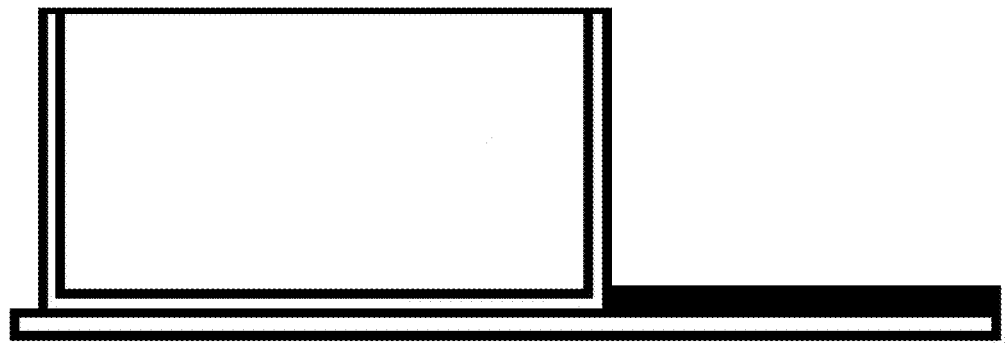
FIG. 5A is a profile/side view taken along line 5A-5A of FIG. 5, to illustrate a preferred height of the vials.

Sample water that is completely (or at least sufficiently) mixed with the colored testing reagents preferably takes on a colored hue (when/if a detectable level of chlorine, acid, or other chemicals are present in pool water), and in certain embodiments of the invention that color/hue can be compared to color indicators on a comparison display 9 located adjacent to the vials (in FIG. 1, a chart of 10 colors is illustrated, with each color corresponding with a test level 8.2, 7.8, 7.6, etc. Persons of ordinary skill in the art will understand that the colors preferably are sufficiently distinct for users to readily match the mixed sample to one of those colors, or "between" two of the colors in the display 9). In some embodiments, generally horizontal vials or chambers 2 can be positioned side-by-side as shown in FIG. 3, and a color indicator/comparison card or panel 11 that is either removable/replaceable or stationary, may be placed between the two vials.

A broad or planar base 10 or other side/feature of the test block preferably is provided to enable the assembly to stand freely without the user having to hold it in its desired "test" position. Although preferably the base is formed or integrally attached to the test kit assembly, persons of ordinary skill in the art will understand that it can be provided in one or more separate brackets or elements configured to cooperate with the rest of the assembly to provide the desired free-standing function. Although a generally rectangular base is illustrated, persons of ordinary skill in the art will understand that it may be provided in any suitable size, shape, position, and/or configuration, including (without limitation) one or more protrusions or leg elements extending laterally from the test kit.

Moreover, in some of the many alternative embodiments of the invention, a broad or planar base may facilitate use of some of the many alternative vial shapes with which the current inventions may be practiced, such as a similarly broad and planar vial (i.e. one resembling a petri-dish) with angular and/or rounded sides. These or other embodiments may further include a vial bottom and/or at least one vial side wall that is white or light in color (opaque or semi-opaque), or that otherwise provides a neutral background that makes reading the true color of the test water easier. This white or light-colored side can be permanently attached/molded to the test kit, or removable (i.e. a white card, perhaps one with information/instructions printed on at least one side). Embodiments using one or more broad and planar vials preferably are configured to allow ready viewing (to determine the color/hue result of the test) from multiple angles, even top/downward viewing.

In certain embodiments, a color comparison panel may further be placed advantageously alongside and/or adjacent to the vial to enhance the ability for users to make a color comparison from the top downward or from some other viewing angle or angles. Further in that regard, persons of ordinary skill in the art will understand that, in still further of the many alternative embodiments of the invention, the color panel/chart can be curved and/or angled with respect to the vials (or can be provided in multiple pieces/planes all within a single kit, such as in a vertical plane generally parallel to the vials and in a horizontal plane generally parallel to the base element), to facilitate viewing from angles other than "straight-on" from the side, or "straight down" from the top.

Persons of ordinary skill in the art will understand that the base can be any suitable size and/or shape (and can be fabricated from any suitable materials) but preferably helps reduce the risk of the unit falling over and spilling water/reagent from the vials/test chambers. As indicated above, although the base preferably is formed integrally with the assembly, persons of ordinary skill in the art will understand that it alternatively can be formed as one or more separate elements configured to cooperate with the rest of the assembly and provide the desired functionality and/or appearance/display/viewability. Again without limitation, legs/braces can be provided that pivot from a closed position alongside the vials to an "open" position extending laterally to support the kit in an upright position.

Persons of ordinary skill in the art also will understand that, if a "record" is desired for the test results, this type of configuration permits the user to set the completed test kit in a convenient location and use their digital camera (or smartphone, other recording device, etc.) to take a photograph or make some other convenient record of the actual mixed/colored water in the test block, and can easily save/transmit/etc. that photographic or other record in any of a wide range of useful ways and to a variety of recipients. Among other things, this process can be used to satisfy any legal requirements for such record-keeping, and also may be used as a management tool for employers desiring to monitor and perform quality checks on the services provided by their employees. It also can be used by pool owners wanting to confirm that their pools are being serviced properly by third party companies or individuals, and even by parents who want to be able to confirm that their kids are properly doing their "pool chores" such as testing and maintaining the chemistry of the pool. Such systems even facilitate remote troubleshooting efforts for pools that, for any variety of reasons, may be experiencing an imbalance in their chemistry—photos of the test results can be easily sent to remote experts/advisors, as part of soliciting advice from the expert/consultant.

Preferably, the invention can be practiced in any of a wide range of combinations and iterations of the features discussed herein. For example, one embodiment provides an improved water chemistry test kit that includes a test block, colored liquid reagents, and color comparison displays. In a preferred embodiment, the test block is formed with vials that are generally horizontal, although persons of ordinary skill in the art will understand that other shapes and orientations may be utilized without departing from the scope of the invention. Also preferably, the mouth at the top of each vial is formed along a substantial portion of the vial's horizontal length/dimension. Preferably, the horizontal and other dimensions of the vials/chambers enable water to move and/or be circulated throughout the vial so that the desired mixing occurs for test purposes. In at least certain embodiments, that moving/motion can approximate a wave or waves rolling from one side of the vial/chamber to the other, and in any case preferably quickly and thoroughly mixes the colored liquid reagents with the sample water. Preferably, adjacent to each vial/chamber is a color comparison display for ready visual analysis of the test results. The test block further preferably has a base that allows it to be freestanding.

Another embodiment of the invention is a test block for a water chemistry test kit. Preferably, the test block has one or more chambers or vials that are shaped in such a way that the sample of test water in them lays in a way that is primarily "horizontal" when the vial is filled to the fill line(s). Preferably, adjacent to each vial is a color comparison display, and a base is provided that allows the assembly to be freestanding in an "upright" position (that allows the test results to be readily viewed without the user to having to hold the block from falling).

Yet another embodiment of the invention is the provision of a water chemistry test kit that includes a test block, colored liquid reagents, and color comparison displays. The test block has vials to hold samples of the water being tested. The vials have one or more set of ridges, walls, semipermeable barriers, etc. within them that causes increased mixing action of the water and chemical reagents, to quickly and thoroughly blend those together when the test block is tilted, tapped, shaken, or otherwise agitated (typically done intentionally and manually by the person who is testing the water).

A further embodiment of the invention is a water chemistry test kit that includes a test block, colored liquid reagents, and color comparison displays. Formed within the test kit are one or more vials for holding/mixing water samples with colored liquid reagents. At least one opening (such as a hole/slot/etc.) is formed or otherwise provided in a wall/side of each vial and is positioned to serve as a drain hole. The lowermost edge of the drain hole is further preferably located at the fill line necessary to conduct the water sample testing, and enables a user to easily fill the vials with sample water to the "proper" level (and readily or effectively "automatically" drain the water to the proper test level). Adjacent to each vial is a color comparison display. The test block further has a base that allows it to be freestanding.

Still another embodiment of the invention is a water chemistry test kit of any of the aforementioned types, that further includes a valve or valves that can be activated manually and/or automatically by any suitable means (such as a button, lever, pin, dial, etc.). Among other things, such a valve element may be added to enable a user to easily drain sample water from the vial down to the proper/desired test level (so that the proper proportion of reagent chemical(s) and water is achieved).

Another of the many alternative embodiments of the invention is an improved water chemistry test kit having any combination of the aforementioned characters, in which the test block is formed with vials that are at least generally horizontal. The mouth at the top of each vial is formed along a substantial portion of the vial's horizontal length. The horizontal dimensions of the vials enable water to move throughout the vial so that a wave or waves roll from one side of the vial to the other and quickly/thoroughly mix colored liquid reagents with sample water. An additional wall, curve or other type of barrier is formed near the top of at least one side of each vial and serves to deflect the wave(s) of water and prevent them from splashing out through the vial's mouth.

One preferred embodiment of the invention provides an improved water chemistry test kit that includes a test block, colored liquid reagents, and color comparison displays. The test block is formed with vials that are at least generally horizontal. The mouth at the top of each vial is formed along a substantial portion of the vial's horizontal length. The horizontal dimensions of the vials enable water to move throughout each vial so that a wave or waves roll from one side of the vial to the other and quickly/thoroughly mix colored liquid reagents with sample water. The vials further have at least one blending element or means for blending (such as a ridge, wall, semipermeable barrier, etc.) within them that cause water and chemical reagents to more quickly and thoroughly blend with each other when the test block is agitated (such as by being tilted, tapped or shaken). At least one hole is formed in a wall/side of each vial and is positioned to serve as a drain hole. The bottom of the drain hole is further located at the fill level necessary to conduct the water sample. A valve or valves activated by a suitable actuator (such as a button, lever, pin, dial, etc.) enables a user to easily drain sample water from the vial down to the proper test level. An additional wall, curve or other type of barrier is formed at or near the top of at least one side of each vial and serves to deflect the wave(s) of water and reduce the risk of or preferably even prevent them from splashing out of the vial through the vial's mouth. Adjacent to each vial is a color comparison display. The test block further has a base or similar element (preferably formed integrally with the block) that allows it to be freestanding.

Among other embodiments, persons of ordinary skill in the art will understand that at least certain aspects of the invention may be practiced with a single test chamber (rather than a "block" of multiple chambers.

The present invention is described herein with reference to the accompanying Figures, which serve as illustrations of some of the many embodiments in which the invention may be practiced. Subject to the context and other factors (including for example the understanding of persons of ordinary skill in the arts relevant to the inventions), generally in those Figures and references similar reference numerals refer to similar or identical elements throughout this description.

Those Figures and references, and the other terminology used in these descriptions, are not intended to be interpreted in any limited or restrictive manner, simply because they are being utilized in conjunction with a detailed description of certain embodiments of the invention. Furthermore, various embodiments of the invention (whether or not specifically described herein) may include one or more of the features disclosed herein, no single one of which (a) is necessarily solely responsible for any particular desirable attribute(s) of the inventions or (b) is essential to practicing the inventions described.

For the purpose of summarizing the invention, certain objects and advantages have been described herein. It is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The apparatus and methods of the invention have been described with some particularity, but the specific designs, constructions, and steps disclosed are not to be taken as delimiting of the invention. A wide range of modifications and alternative structures and steps for practicing the invention will make themselves apparent to those of ordinary skill in the art, all of which will not depart from the essence of the invention, and all such changes and modifications are intended to be encompassed within the appended claims.

Although the examples of the many various methods of the invention are described herein with steps occurring in a certain order, the specific order of the steps, or any continuation or interruption between steps, is not necessarily intended to be required for any given method of practicing the invention.

What is claimed is:

1. Apparatus for water chemistry testing, including:
a test block having a planar base;
at least one mixing chamber formed within said test block, said mixing chamber having a generally horizontal orientation and comprising at least one drain port for draining water out of said mixing chamber;
a mouth opening by which said mixing chamber is filled by submerging said mixing chamber into the water to be tested and allowing that water to flow through said mouth opening to eventually fill said mixing chamber;
at least one drain opening formed in a wall of said at least one mixing chamber, a lowermost edge of said drain opening positioned at a fill line which indicates a desired volume of liquid for testing, said drain opening configured to allow liquid to drain from the drain opening and out of said drain port of the mixing chamber until the desired volume is reached within the mixing chamber;
the mixing chamber further including at least one valve configured to control water flow through said drain port and said drain opening; and
at least one set of mixing structures located within the mixing chamber, said mixing structures configured to increase mixing of water and chemical reagents within the mixing chamber.

2. The apparatus of claim 1, including a plurality of such mixing chambers.

3. Apparatus for water chemistry testing, including:
a test block having a planar base and at least one generally horizontally-oriented mixing chamber formed therein, said mixing chamber having a generally vertical sidewall, said sidewall including at least one drain opening therethrough, said at least one opening positioned adjacent a fill line that indicates a desired volume of liquid for testing and configured to allow an excess volume of liquid to drain out of said mixing chamber through a port provided in said mixing chamber;
one or more sets of barrier elements positioned within the mixing chamber and configured to increase mixing turbulence of water with chemical reagents in the mixing chamber; and
a comparison display element adjacent the mixing chamber configured to provide a visual comparison with the color of the water in the mixing chamber.

4. Apparatus for water chemistry testing, including:
at least one liquid flow interrupter element positioned in a mixing chamber to enhance the intermixing in the mixing chamber of chemical reagents that are added to the liquid being tested in the mixing chamber;
wherein said mixing chamber is configured to enable the liquid to move throughout the mixing chamber in a wavelike rolling motion to further enhance the intermixing of the liquid with chemical reagents in the mixing chamber;
said mixing chamber comprising one or more drain elements for adjusting the volume of liquid within the mixing chamber by allowing liquid to drain out of the mixing chamber until a desired volume of liquid for testing is reached; and
wherein said mixing chamber is formed within an upright test block assembly.

5. The apparatus of claim 4, including:
at least one mixing chamber having a generally horizontal orientation, said at least one mixing chamber having at least one drain opening positioned adjacent a fill line that determines a desired volume of liquid for testing.

6. A method of water chemistry testing, including the steps of:
providing the apparatus of claim 1 or claim 3 or claim 4 or claim 5;
filling the mixing chamber or chambers with water to be tested;
adding at least one chemical reagent to the mixing chamber;
analyzing the results of the test by comparing the color of the water in the mixing chamber to a color chart provided on the apparatus.

7. The apparatus of claim 4, in which:
said mixing chamber has a generally horizontal orientation, and said at least one liquid flow interrupter element is positioned on a sidewall of said mixing chamber, and said apparatus is sized and configured to permit a user to tilt same from side to side to mix the liquids within the mixing chamber.

8. Apparatus for water chemistry testing, including:
a freestanding test block assembly having an integrally formed base, the test block assembly comprising:
at least one mixing chamber having a generally horizontal orientation and comprising at least one drain port for draining water out of said mixing chamber;
at least one opening formed in a vertical sidewall of said at least one mixing chamber, a lowermost edge of said opening positioned at a fill line which indicates a desired volume of liquid for testing, said opening configured to allow liquid to drain from the opening and out of said drain port of the mixing chamber until the desired volume is reached within the mixing chamber;
the mixing chamber further including at least one valve configured to control water flow through said drain port and said opening;
at least one barrier element positioned within the mixing chamber and configured to increase mixing turbulence of water with chemical reagents in the mixing chamber; and
a comparison display element adjacent the mixing chamber configured to provide a visual comparison with the color of the water in the mixing chamber.

9. The apparatus of claim 1 or claim 3 or claim 4 or claim 8, wherein said mixing chamber is non-collapsible.

10. The apparatus of claim 3 or claim 4 or claim 8, wherein said mixing chamber provides a fixed-volume measuring reservoir for obtaining a desired volume of liquid for testing, further including at least one opening by which said mixing chamber can be repeatedly refilled with water to be tested.

11. Apparatus for water chemistry testing, including:
at least one mixing chamber having a generally horizontal orientation, wherein the mixing chamber is maintained in the horizontal orientation by an upright test block assembly;
a mouth opening by which said mixing chamber is filled by submerging said mixing chamber into the water to be tested and allowing that water to flow through said mouth opening to eventually fill said mixing chamber; and
at least one drain opening formed in a wall of said at least one mixing chamber, a lowermost edge of said drain opening positioned at a fill line which indicates a desired volume of liquid for testing, said drain opening configured to allow liquid to drain from the drain opening and out of the mixing chamber until the desired volume is reached within the mixing chamber.

12. Apparatus for water chemistry testing, including:
a test block assembly having at least one mixing chamber having a generally horizontal orientation, said test block assembly being supported by a base element;
at least one opening formed in a wall of said at least one mixing chamber, wherein said mixing chamber is filled by submerging said mixing chamber into the water to be tested and allowing that water to flow through said opening to eventually fill said mixing chamber; and
a lowermost edge of said opening positioned at a fill line which indicates a desired volume of liquid for testing, said opening configured to allow liquid to drain from the opening and out of the mixing chamber until the desired volume is reached within the mixing chamber.

13. A test block assembly, including:
a test block having a planar base;
at least one mixing chamber formed within said test block, said mixing chamber having a generally horizontal orientation and having at least one opening by which said chamber is filled when said chamber is submerged into a liquid to be tested.

14. The test block assembly of claim 13, said mixing chamber further including at least one drain port for draining water out of said mixing chamber.

15. The test block assembly of claim 13, further including at least one drain opening formed in a wall of said at least one mixing chamber, a lowermost edge of said drain opening positioned at a fill line which indicates a desired volume of liquid for testing, said drain opening configured to allow liquid to drain from the drain opening and out of said drain port of the mixing chamber until the desired volume is reached within the mixing chamber.

16. The test block assembly of claim 15, wherein the mixing chamber further includes at least one valve configured to control water flow through said drain port and said drain opening.

17. A test block assembly, including:
a test block having a planar base;
at least one mixing chamber formed within said test block; and
at least one set of mixing structures located within said mixing chamber, said mixing structures positioned and configured to increase mixing of water and chemical reagents within said mixing chamber.

* * * * *